United States Patent
Rida et al.

(10) Patent No.: US 9,689,881 B2
(45) Date of Patent: Jun. 27, 2017

(54) METHOD FOR SEPARATING TARGET MOLECULES OR PARTICLES FROM FIBRINOGEN-CONTAINING SAMPLES INCLUDING BLOOD COMPONENTS

(75) Inventors: Amar Rida, Chavannes-Remens (CH); Nicolas Mermod, Buchillon (CH); Patrice Francois, Cran-Gevrier (FR); Vladimir Lazarevic, Renens (CH); Jacques Schrenzel, Geneva (CH)

(73) Assignee: Spinomix S.A., Lausanne (CH)

( * ) Notice: Subject to any disclaimer, the term of this patent is extended or adjusted under 35 U.S.C. 154(b) by 433 days.

(21) Appl. No.: 13/822,209

(22) PCT Filed: Sep. 15, 2011

(86) PCT No.: PCT/IB2011/054035
§ 371 (c)(1),
(2), (4) Date: Mar. 11, 2013

(87) PCT Pub. No.: WO2012/035508
PCT Pub. Date: Mar. 22, 2012

(65) Prior Publication Data
US 2013/0164737 A1    Jun. 27, 2013

(30) Foreign Application Priority Data

Sep. 15, 2010  (CH) ........................ 1478/10
Dec. 7, 2010   (CH) ........................ 2041/10
Jul. 20, 2011  (CH) ........................ 1207/11

(51) Int. Cl.
| | | |
|---|---|---|
| G01N 33/86 | (2006.01) | |
| G01N 33/569 | (2006.01) | |
| C12Q 1/56 | (2006.01) | |

(52) U.S. Cl.
CPC .............. *G01N 33/86* (2013.01); *C12Q 1/56* (2013.01); *G01N 33/56938* (2013.01); *G01N 2333/75* (2013.01); *G01N 2333/974* (2013.01)

(58) Field of Classification Search
None
See application file for complete search history.

(56) References Cited

U.S. PATENT DOCUMENTS 6,680,195 B1 *   1/2004  Patti et al. ................. 435/320.1
2003/0068662 A1 * 4/2003  Fournier .......... G01N 33/56938
                                              435/7.32

FOREIGN PATENT DOCUMENTS

| EP | 1400589 A1 | 3/2004 |
|---|---|---|
| EP | 1861495 A1 | 12/2007 |
| WO | WO-9515397 A1 | 6/1995 |
| WO | WO-2009015484 A1 | 2/2009 |
| WO | WO-2011007004 A1 | 1/2011 |
| WO | 2012/035508 | 3/2012 |

OTHER PUBLICATIONS

Watson, K.C. 1978 Journal of Clinical Microbiology 7(2): 122-126.*
Escamilla et al., "Evaluation of Blood Clot Cultures for Isolation of *Salmonella typhi*, *Salmonella paratyphi*-A, and *Brucella melitensis*," J. Clin. Microbiol., 24(3):388-390 (1986).
Francois et al., "Identification of plasma proteins adsorbed on hemodialysis tubing that promote *Staphylococcus aureus* adhesion," J. Lab Clin. Med., 135(1):32-42 (2000).
Greene et al., "Adhesion properties of mutants of *Staphylococcus aureus* defective in fibronectin-binding proteins and studies on the expression of fnb genes," Mol. Microbiol., 17(6):1143-1152 (1995).
Vaudaux et al., "Increased Expression of Clumping Factor and Fibronectin-Binding Proteins by hemB Mutants of *Staphylococcus aureus* Expressing Small Colony Variant Phenotypes," Infection and Immunity, 70(10):5428-5437 (2002).

* cited by examiner

*Primary Examiner* — Marsha Tsay
(74) *Attorney, Agent, or Firm* — McAndrews, Held & Malloy, Ltd.

(57) ABSTRACT

A method for separating target molecules or particles from a fibrinogen containing sample comprises: (a) trapping the said target molecules or particles in a fibrin network by converting at least partially the fibrinogen contained in the sample into fibrin; (b) retracting the said fibrin network to form a fibrin clot; (c) separating the said fibrin clot from the surrounding sample medium.

24 Claims, 6 Drawing Sheets

METHOD FOR SEPARATING TARGET MOLECULES OR PARTICLES FROM FIBRINOGEN-CONTAINING SAMPLES INCLUDING BLOOD COMPONENTS

RELATED APPLICATIONS

This application is a national stage application, filed under 35 U.S.C. §371, of International Application No. PCT/IB2011/054035, filed Sep. 15, 2011, which claims priority to Swiss application No. 01478/10, filed Sep. 15, 2010; to Swiss application No. 02041/10, filed Dec. 7, 2010; and to Swiss application No. 01207/11, filed Jul. 20, 2011, each of which are herein incorporated by reference in their entireties.

FIELD OF THE INVENTION

The invention relates to a method for sample processing for the separation of target molecules or particles from the said sample. More specifically, the invention concerns a sample preparation procedure allowing effective separation and concentration of target molecules or particles from samples containing fibrinogen proteins prior to their detection and analysis.

DESCRIPTION OF RELATED ARTS

In bioassays the ability to extract, concentrate and purify target molecule(s), particle(s) or analyte(s) from diverse samples (i.e. sample preparation) represents a critical step and is challenging as a prerequisite step for effective target detection and analysis. The sample preparation step is the major rate-limiting step in bioassays in terms of detection limit, reproducibility and interferences with other compounds of said particle(s) or analyte(s). Existing sample preparation procedures typically involve lengthy manual or complex robotic pipeting steps including long centrifugation rounds. Not only are such procedures slow, costly and labor consuming they also can represent a health risk to the laboratory staff demanding expensive disposal of hazardous chemicals. Moreover, the workflow for sample preparation, especially for the new generation of molecular targets has become even more complex and multiple solutions are being offered. Currently, different and individual solutions for sample preparation are being used for each sample type and target. Providing a standard sample preparation workflow solution applicable for multiple samples and targets that are easy-to-implement, compatible with automation and reagent integration and involving minimal hands-on time, still remains an unresolved requirement in the life sciences and diagnostic setting. Further, standardization of sample workflow methodologies is a major requirement mainly in the regulated diagnostic environments.

A typical illustration of the complexity of the sample preparation is the detection of target molecules or particles out of the complex blood medium. Particularly complex is the detection of infectious agents (bacteria, fungi) from blood at low detection levels. At the clinical level, the detection of blood infection (i.e. Sepsis) is particularly important as it is the cause of a serious medical condition induced by inflammatory response to microbial infection in blood. Sepsis represents indeed the most common cause of death in intensive care units. Moreover, due to the inferior detection of microorganisms from blood, the missing or delayed identification of the infectious agent and/or the absence or delayed antibiotic susceptibility testing, many antibiotic treatment modalities are being initiated only empirically without appropriate diagnostic coverage. The medical need in sepsis diagnostics for an early detection, fast microorganism identification and antibiotic susceptibility testing and adequate patient management is highly unmet. At times of increasing resistance development of microorganisms (e.g. nosocomial microorganisms), new methodologies for rapid and accurate sepsis diagnostics are crucial to decrease morbidity and mortality. Finally, another source of sepsis infections are blood transfusions. Effective detection of microorganisms out of blood, blood components and blood derivatives is of high importance for prevention of contaminations.

The use of blood cultures, either as blood bottle culture or blood agar culture still is the routine method of choice (gold standard) to detect and identify infectious agents in patients with bacteremia and sepsis.

A major issue in the detection of bacterial cells in the blood is the ability of detecting cell numbers as low as 1 Colony Forming Units (CFU) per milliliter. In this context, the volume of blood that must be processed at a detection level in this order of magnitude must therefore consist of several milliliters (5-10 ml) of the blood specimen. 'Looking for a needle in a haystack', the big challenge in blood infection diagnosis will be based on the availability of efficient and easy-to-implement technologies that allow the extraction and purification of specific infection biomarkers from viable micro-organisms or their nucleic acids genetic content.

As for instance reported in the international patent applications WO95/15397 and WO2009/015484, multi-centrifugation or filtration methodologies are used in combination with specific cell wall/membrane lysis steps for enriching target microorganisms out of blood samples and body fluids. Next to low enrichment efficiency, another limitation of such centrifugation methodologies is their non-compatibility with routine automated laboratory assay work flows. In order to overcome the process limitations of centrifugation, magnetic particles coated with affinity groups directed against target microorganisms have been introduced. Using a magnetic force the particles capture the targets on their surfaces resulting in the easy separation of the targets out of blood. However, there are some major disadvantages for a broad application of affinity groups on magnetic beads to capture viable bacteria. First, the spectrum of pathogenic microorganisms consists of a long list of gram-negative and gram-positive bacteria and numerous fungi species; there are no generic affinity groups available that cover all classes of microorganisms. Also, many such microorganisms are encapsulated, a phenomenon that facilitates their survival and disposition in blood. Secondly, it has been shown that microorganisms are not always free-floating in the bloodstream but are rather associated to or sequestered from some blood cells as well as from platelets. In case of *Staphylococcus aureus* for instance, the interaction platelets and further sequestration of the bacteria by the platelets is an important virulence factor that allows bacteria to escape the host defense system.

An alternative to the direct enrichment of viable microorganisms out of blood samples consists of the use of molecular biomarkers (specific nucleic acid gene sequences) and immediate subsequent nucleic acid amplification techniques, such as PCR (Polymerase Chain Reaction). The method opens new possibilities to deliver faster results. However, the level of detection (sensitivity) is often lower than that of culture-based methods. The limited sensitivity of the molecular methods is mainly related to the high background DNA from eukaryotic cells (white blood cells) in the blood sample. An increase of the sensitivity of the PCR-based methods can be achieved by drawing out the eukaryotic nucleic acids from the blood sample or by specifically concentrating the microorganism (prokaryotic) DNA. In this perspective, EP-A-1,400,589 discloses a method of separating the prokaryotic DNA from blood lysate comprising the step of specific binding of prokaryotic DNA with at least one protein or polypeptide followed by the separation of the so-formed complex. Within the same scope, EP-A-1,861, 495 describes a method for specifically isolating nucleic acids from microbial cells provided in a mixed sample which additionally comprises higher eukaryotic cells. This invention disclose the use of nucleases, especially DNA-degrading nucleases, for degrading nucleic acids in the presence of one or several chaotropic agents and/or one or several surfactants in whole blood, allowing thereby to draw out eukaryotic nucleic acids from blood lysates. Both methods are limited by the complex protocols and the timely processing steps, i.e. half a day before obtaining purified bacterial nucleic acids. Moreover, these methods show a limit of detection of 100 CFU/ml which is still considerably lower than the sensitivity of the blood culture method that by definition is 1 CFU in the considered 10 ml volume Besides the mentioned limitations of the-state-of-the-art nucleic acids detection methods, the relevance of molecular methods for detecting bacteria and fungi in general is questionable. In fact, detecting circulating DNA in blood does not necessarily correlate with the blood culture methods that detect viable microorganisms. To "keep" such correlation, some approaches propose the identification of the infectious agents using molecular based methods starting from positive blood cultures. However, the clinical relevance of such approaches remains limited because the time-consuming culture method is still required. This question is even of higher importance as the molecular methods fail in the vast majority of cases to provide information on the antimicrobial susceptibility spectrum of the bacterium, the latter still relies on the traditional culture approaches.

Knowing these shortcomings, the development of new methods allowing fast and reliable microorganism detection and identification in the blood remains a highly relevant question. Moreover, the detection of infectious agents in blood presented herein is a typical example to illustrate the complexity of sample preparation procedures and their major importance in bioassays in general and medical diagnostics in particular. Assays for determining the presence of target molecules or particles in a variety of samples, including food, clinical, environmental, and experimental samples, are of increasing importance.

SUMMARY OF THE INVENTION

The invention relates to a method for sample preparation and processing resulting in an effective separation of target molecules or particles from a surrounding complex liquid medium. This method will further allow to recover the said target(s) highly concentrated in a controlled buffer medium, at a volume that is preferably at least $\frac{1}{10}$ of the initial sample volume. Furthermore, the advantage of the disclosed method is the capability to reach a concentration rate of $\frac{1}{100}$ to $\frac{1}{1000}$ of the initial sample volume. The so concentrated target(s) can be thereafter preceded very easily through further purification step(s) and/or directly analyzed using state-of-art methodologies.

The disclosed sample preparation method is particularly adapted to be used with diverse sample sources and a broad spectrum of volume sizes. Furthermore, the separation according to the invention allows to specifically or un-specifically separate the target particle(s) or molecule(s) from complex sample volumes using size and/or affinity selection.

Accordingly, this invention discloses a sample preparation method that presents therefore the advantage to be universally used for virtually any type of sample and target.

Based on the disclosed method this invention further discloses a sample collection device that can be very easily used manually or integrated with state-of-the-art automated systems which makes this sample preparation method therefore easily to be integrated in routine laboratory work flows.

The technical basis of the disclosed sample preparation method is based on the inventors' observation about the possibility of efficiently separating target micro-organisms, like bacterial or fungi particles, typically from blood samples by converting, in a controlled and standardized way, fibrinogen to fibrin through controlled coagulating the blood sample using the thrombin enzyme to trap said target particles within a fibrin network that will rapidly retract to form a small pellet within the blood container. As the pellet will be formed, the surrounding blood sample can be decanted leading to separation of the targets trapped within this small pellet. In a second step, the pellet can be lysed to recover the targets from their fibrin trap within a small volume of a controlled buffer. By this process the smallest size of the pellet is a key factor that needs to be controlled as it will determine the concentration rate of the disclosed method.

Accordingly, by blood sample one refers to whole blood, platelet-rich plasma, and platelet-poor plasma or serum. Blood according to the invention, can obviously also refer to blood substitutes or artificially composed sample constituted from blood components, blood additives or any other components that mimic blood functions. Typical example of such blood components and that are usually used in blood transfusions include, platelet concentrates, red cell (hemoglobin) concentrates, serum or plasma substitutes (also known as volume expanders). In case where the said blood sample is deficient of clotting factors (mainly fibrinogen) as for instance in some clinical cases like sepsis samples, composed blood samples or blood substitutes, this deficiency can be compensated by adding clotting factors including fibrinogens to the said blood sample as a mandatory component to be able to separate target particles or molecules according to the invention.

Although the current invention preferably discloses a method of separating of microorganisms or infectious molecules or particles from a sample of blood, it is acknowledged by a skilled person in the art that the sample of blood herein can also refer to a composed sample that includes blood constituents entering into the controlled coagulation process as described previously.

Accordingly, in general the invention discloses therefore a method of separating and concentrating target particles or molecules from samples containing fibrinogen proteins by trapping, in a first step, the said target molecules or particles in a fibrin network by converting at least partially the fibrinogen contained in the said sample into fibrin to form the fibrin network. In a second step, the so formed fibrin network to form a fibrin clot that will be separated from the surrounding sample medium.

In one embodiment, the separation according to the invention is obtained by size selection by trapping the said target particle. In this trapping process, the size of the fibrin network pore is therefore particularly critical. The smaller pore size will indeed lead to a more efficient trapping of small infectious microorganisms like *E. coli* (2 µm) or *Chlamydia* (0.3 µm) or even viruses. In this respect, the control of the trapping fibrin network can be realized by adjusting parameters like sample pH and ionic strength and the concentrations of calcium, fibrinogen, thrombin within the said sample.

In one embodiment, the separation according to the invention is obtained by affinity trapping the said target particle in the fibrin network. The inventors' observation is that bacterial particles like *Staphylococcus aureus* have a strong affinity to fibrinogen/fibrin molecules, which further facilitate (enhance) their separation and concentration according to the invention method. By mimicking affinity interaction of bacterial particles, the invention discloses to use native as well as induced affinity interactions to separate targets from fibrinogen contained samples.

The induced affinity separation according to a preferred embodiment of the invention is realized with fibrinogen recombinant protein(s) composed of fibrinogen fusion protein(s) comprising a capturing moiety domain directed against the said target molecules or particles. In another embodiment chemical trapping is assured by a fibrin/fibrinogen-binding moiety like a *Staphylococcus aureus* fibrinogen binding protein and a substance-capturing moiety like an antibody directed against the said target molecules or particles.

Accordingly, size trapping within the fibrin network as well as specific affinity binding reactions may be employed for the determination or isolation of a wide range of target substances in biological samples. Examples of target substances are cells, cell components, cell subpopulations (both eukaryotic and prokaryotic), bacteria, viruses, parasites, antigens, specific antibodies, toxins, proteins, nucleic acid sequences and the like.

Fibrinogen as referred herein can be therefore a natural fibrinogen obtained from any blood source as for instance human blood or vertebrate blood in general. Fibrinogen according to the invention can be also a synthetic composed molecule obtained by combining natural fibrinogen with any other molecule in a way to obtain a new molecule with new affinity functionality for instance. In a preferred embodiment, the so-combined molecule is obtained by a covalent bonding of a fibrinogen molecule to another molecule. In another embodiment, the so-combined molecule is a fusion protein produced by the state-of-art recombinant protein synthesis techniques.

Fibrinogen as referred herein can be also to a synthesized fibrinogen molecule modified that will have the entire fibrinogen crystal structure. In a preferred embodiment the synthesized fibrinogen molecule is a modified molecule that will have a different structure, size, composition and affinity activities. More particularly, it is desirable that the fibrinogen according to the invention is a simplified structure molecule (instead of the complex large natural fibrinogen molecule) that still expresses the cleavage (polymerization) activity by thrombin and that can have a defined affinity binding reaction to target particle(s) or molecule(s).

The invention discloses therefore the use of fibrinogen or fibrinogen modified proteins as a vehicle to trap or capture target particle(s) or molecule(s). Upon the exposure of the said fibrinogen or fibrinogen modified proteins to thrombin cleaves the fibrinogen molecules and their transformation to fibrin. The fibrin particles will thereafter self-polymerize to form a small clot in which the targets are trapped resulting therefore to the separation of the target out of the sample liquid volume. The proposed method presents a large advantage when compared with the state-of-art techniques as magnetic particles for instance or any other "solid surface" based technologies. As it occurs at the molecular level, the reaction between the targets and the fibrinogen vehicle is very fast and efficient and the non-specific binding issues inherent to surface based assay will be eliminated.

Based on that and in a particular use, the present invention provides a method that allows to provide a solution of effectively separating and concentrating of intact microorganisms from an infected blood sample. An attainable aim of this is the separation of minute amounts of microorganisms from large volumes of blood allowing thereafter their concentration in a small volume of buffer compatible with further processing steps. Another attainable aim of this invention is the separation of intact microorganisms from a blood sample that can be subsequently detected and analyzed by specific techniques recognized in the art. As achieved, instead, this method opens many possibilities in rapid and effective detection and diagnosis of bloodstream infections using fast culture methods as well as rapid and more sensitive molecular based assays.

It becomes therefore clear that from the previous description that fibrinogen according to the invention can be native to the sample (i.e. whole blood samples) or artificially added to the said sample.

Based on that and in a particular use, the present invention provides a method for separating target molecule(s) or particle(s) from a composed sample, which comprises the steps:
  (a) Adding fibrinogen to said sample.
  (b) Trapping the said target molecules or particles in a fibrin network by converting the fibrinogen added in the said sample into fibrin to form the fibrin network.
  (c) Retracting the said fibrin network to form a fibrin clot.
  (d) Separating the said fibrin clot from the surrounding sample medium.

A composed sample according to the invention may include, blood, blood derivatives or blood components samples, but also can refer to any fibrinogen free sample as for instance but not limited to, clinical (like urine, sputum and swab), food and environmental samples.

Accordingly, the invention further discloses a sample collection device for separating target molecules or particles from a sample, comprising: (i) an identification code; (ii) a container for containing the said sample; and (iii) a fibrinogen-containing sample in the container, the device being operable to form a fibrin clot that traps in a separable manner the said target molecules or particles upon the exposure of the said sample to thrombin or a thrombin-like enzyme within the said device.

The device according to the invention can be a standard reaction tube or reservoir designed to receive a fluid sample that need to be thereafter examined for the existence of target particle(s) or molecule(s) as for instance for pathogenic particle(s) (bacteria, viruses etc.) or target molecule(s) (DNA, RNA or protein etc.). The device of the invention will further include stable reagent formulations that will lead to the fibrin clot formation and targets separation as previously described herein. Preferably, the device includes a reaction area containing its stored stable reagent formulations that include clotting factors as fibrinogen molecules and coagulation promoting agents as thrombin enzymes. Such device will allow the quantitative isolation and detection of targets like infection agents, toxin, nucleic acids and proteins in a test kit, at extremely low copy numbers from any complex biological sample. The fact that the disclosed device will allow to collect the sample and at the same time to effectively separate and concentrate targets particles or molecules out of the said sample will considerably simplify the necessary sample processing steps and further result in a reduction of potential risks of infection and risks of contamination.

Accordingly, a main aspect of the invention concerns a method for separating target molecules or particles from a fibrinogen containing sample, attained according to independent claim 1.

Accordingly, a main aspect of the invention concerns a sample collection device for separating target molecules or particles from a fibrinogen containing sample.

Different embodiments are set out in the dependent claims. The subject matter of the claims and all claimed combinations is incorporated by reference in this description and remains part of the disclosure event if claims are abandoned

BRIEF DESCRIPTION OF THE DRAWINGS

The objects and features of the present invention are set forth with particularity in the appended claims. The present invention, both as to its organization and manner of operation, together with further objects and advantages, may best be understood by reference to the following description, taken in connection with the accompanying drawings, wherein

DETAILED DESCRIPTION OF THE INVENTION

Figure 1:
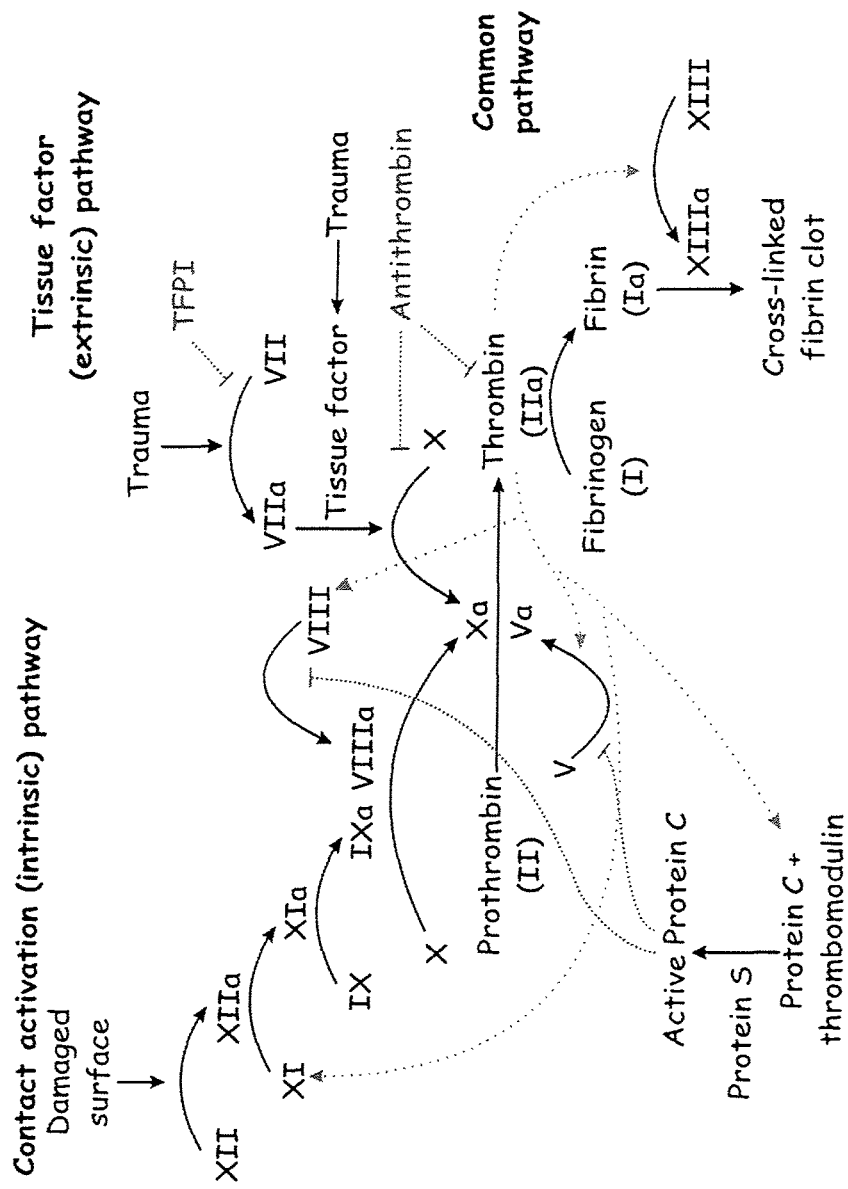
FIG. 1 is a schematic representation of the coagulation process (Ref. http://en.wikipedia.orq/wiki/Coagulation) and that shows the fibrinogen conversion to fibrin that can be used to attain the main aim objective of the invention.
Figure 2:
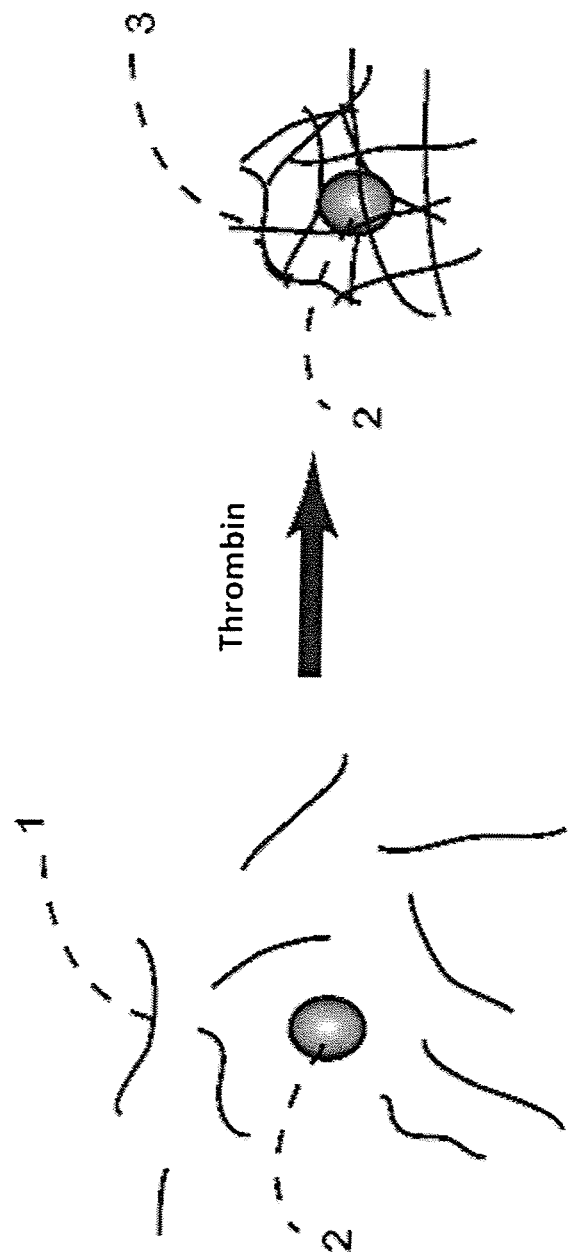
FIG. 2 is a schematic representation of the trapping mechanism of target molecule(s) or particle(s) (2) in a fibrin network (3) upon the exposure of a fibrinogen (1) containing sample to thrombin.

According to one embodiment of the present invention, a method for separating target molecules or particles from a blood sample comprises:
(a) Trapping the said target molecules or particles in a fibrin network by converting at least partially the fibrinogen contained in the said sample into fibrin to form the fibrin network;
(b) Retracting the said fibrin network to form a fibrin clot;
(c) Separating the said fibrin clot from the surrounding sample medium.

Accordingly, by blood sample one refers to whole blood, platelet-rich plasma, and platelet-poor plasma. Blood sample can also refer to serum where in this condition fibrinogen must be added to the said sample to allow the separation mechanism working according to the invention. Blood according to the invention, can obviously also refer to blood substitutes or artificially composed samples constituted from blood components, blood additives or any other components that mimic blood functions. Typical example of such blood components and that are usually used in blood transfusions include, platelet concentrates, red cells (hemoglobin) concentrates, serum or plasma substitutes (also known as volume expanders). In case where the said blood sample is deficient in clotting factors (mainly fibrinogens) as for instance in some clinical cases like sepsis samples, composed blood samples or blood substitutes, this deficiency can be compensated by adding clotting factors including fibrinogens to the said blood sample as a mandatory component to be able to separate target particles or molecules according to the invention.

Within the same spirit, blood sample according to the invention can therefore refer also to an artificially composed blood sample obtained by combining a blood sample with a fibrinogen deficient sample. Such fibrinogen deficient sample can include samples from any sources as for instance biological, clinical, food and environmental samples. More particularly, the term blood sample according to the invention encompasses an artificially composed blood sample by combining clotting factors that at least includes fibrinogens with a fibrinogen deficient sample.

"Fibrin network" as generally used herein means the product of a process in which fibrinogen is cleaved upon the exposure to thrombin enzyme and converted into fibrin. Once the fibrinogen is converted into fibrin, a self-polymerization step occurs in which the fibrin monomers come together and form a non-covalently cross-linked three-dimensional polymer network. Further, in the presence of coagulation factor XIII the fibrin network will be cross-linked by factor XIIIa, a transglutaminase activated by thrombin of the factor XIII. Other transglutaminases exist and may also be involved in covalent cross-linking and grafting to the fibrin network.

"Clot formation and retraction" as generally used herein means the observed pull-in of the fibrin matrix to form a clot after a certain time. The size of this clot can be, under certain condition, reduced over time (i.e. clot retraction) by pulling water out of the clot. Naturally, the clot retraction is induced by release of multiple coagulation factors from activated platelets trapped in the fibrin mesh of the clot.

For the formation of the fibrin network, the concentrations of the fibrinogen solution and/or the thrombin solutions have a significant effect on the density of the formed network, clot formation, cross-linking and speed of the final fibrin matrix. Typically, the reduction of the amount of thrombin and fibrinogen slows down the cross-linking process and contributes to form a fibrin clot with a less dense network. Accordingly, controlling the ratio of the amounts of thrombin and fibrinogen, leads to a controlled formation of the fibrin network density and size of the final clot. Furthermore, the ratio of the amount of thrombin to fibrinogen provides fibrin matrices with a less dense network which is more suitable for target capturing. Moreover, the ratio of the amount of thrombin to fibrinogen provides a retracted fibrin clot with smaller size allowing to attain a high concentration rate of the separated target particles or molecules.

The mechanism underlying the invention is that converting fibrinogen into fibrin leads to the formation of a fibrin network that will play the role of a network that will capture the target particles or molecules. To obtain the desired effect, the control of the said fibrin network formation is particularly important. With this respect, the concentration of thrombin and fibrinogens as the key coagulation factors are critical in the formation of the fibrin trapping network and consequently the clot creation and separation according to the invention. In fact, a high concentration of thrombin and fibrinogens leads to a very dense fibrin network and a large clot size which is not desirable. However, the finding is that lower concentrations of thrombin and fibrinogen lead to the formation of a relaxed fibrin network that retracts rapidly to a small pellet formation in the sample vessel or container. During this retraction, the fibrin network traps the target particles or molecules from the sample volume, leading thereby to their concentration and separation from the said sample.

To reach the desired affects in effectively trapping and separating the target particles or molecules from a sample containing fibrinogen, the concentration of the said fibrinogen in the sample is preferably at least 0.1 µg/ml. In a preferred embodiment the concentration of the fibrinogen in the sample is between 10 mg/ml to 10 µg/ml. Using higher concentration, even exceeding the ranges mentioned herein, can also be used but resulting in a higher fibrin matrix density and retracted clot size. In case of separating target particles using size selection or size trapping using a relatively high concentration of fibrinogen is particularly suited. The smaller the size of the target particle(s) the higher is the requested fibrinogen concentration. However, the downside of using higher concentrations of fibrinogen is the formation of a larger clot size, resulting in a lower concentration rate of the target particle(s). Therefore, in practice and in case of a size selection or size trapping, the concentration of fibrinogen must be optimized in a way to reach maximum capture efficiency and at the same time a lower clot size.

It well understood from the previous description that fibrinogen according to the invention can be native to the sample (i.e. blood samples) or artificially added to the said sample. In a preferred embodiment, fibrinogen will be added to a sample even if the said sample has native fibrinogen, as it is the case of whole blood for instance. This will be for instance advantageous to compensate any fibrinogen deficiency or variation in the concentration of the native fibrinogen that may occur in such samples. In another preferred embodiment, the fibrinogen added to a blood sample (even if the native fibrinogen concentration is at the desired concentration) will be originated from a blood source of a different species than of the sample under consideration. For example, if a human whole blood sample is used one can, according to this embodiment, add a fibrinogen originated from another vertebrate like bovine, sheep, opossum or chicken to the said human sample. Using the fact that fibrinogen/thrombin reaction maybe species specific, one desired effect by using different fibrinogen source as an additive to a sample with native fibrinogen is to specifically use the added fibrinogen (preferably activated with the related species thrombin) to accomplish the target separation while avoiding (minimizing) the interference of the native fibrinogen in the separation process. This can be particularly advantageous as it will permit a more effective control of the separation process of the target(s) and avoids relying on the native fibrinogen variations. Within the same spirit, in another embodiment the added fibrinogen will be a recombinant fibrinogen protein specifically designed to be not cleavable by the endogenous thrombin of the blood sample under use.

The desired effect of effectively trapping and separating the target particles or molecules from a sample containing fibrinogen can be accordingly achieved by subjecting the said sample to thrombin or thrombin-like enzymes. With this respect, the said thrombin can be an exogenous (artificially added to the said sample) or an endogenous (already part of the said sample) thrombin or thrombin-like enzymes. Accordingly, the thrombin can be in active form or generated through activation of coagulation factors like the factor X as shown in FIG. 1. The origin of this thrombin and/or coagulation factors can be from human, animal or insect sources. Accordingly, by thrombin-like enzymes one refers to the family of serine proteases obtained from outside blood sources and that have the ability to convert fibrinogen to fibrin. Such enzymes are well known in the art and usually obtained from snake venom or produced in recombinant form.

In a preferred embodiment, the thrombin concentration is 0.01 to 10 I.U/ml and preferably within the range of 0.1 to 2 I.U/ml of sample. In practice, the quantity of the thrombin or thrombin like enzyme must be rather adjusted in correspondence to the fibrinogen concentration within the device to obtain the desired fibrin network structure and clot size. With this respect, the thrombin amount is preferably less than 20 I.U thrombin per mg of fibrinogen, preferably in a range between 0.01 to 10 I.U thrombin per mg of fibrinogen, more preferably between 0.1 to 1 I.U thrombin per mg of fibrinogen.

In a preferred embodiment to control the fibrin network structure in order to trap target molecules or particles from a sample, the concentration of calcium can also be adjusted. In practice this can be achieved by adding a calcium ion source to the testing sample. The calcium ion source is preferably Calcium Chloride ($CaCl_2$), preferably in a concentration range between 1 to 10 mg per ml of sample volume, even more preferably between 4 to 7 mg per ml of sample volume, most preferably between 5 to 6 mg per ml of sample volume. In blood samples, for instance, calcium is naturally present and the adjustment of the calcium concentration can be achieved by further adding calcium chelating agents selected from the groups of GDTA, EDTA and citrate.

In a preferred embodiment to control the fibrin network structure in order to trap target molecules or particles from a sample, the method may involve the step of adding clotting factor XIII to the said sample. Clotting factor XIII is an enzyme capable of catalyzing the fibrin matrix cross-linking formation after it has been activated by thrombin. This will further help to stabilize the fibrin network structure, accelerate the clot retraction and contribute to titer the fibrin porosity. Such factor XIII in its inactive or active (XIIIa)

formats may be added or adjusted along with the fibrinogen additive in a concentration range between 0.5 to 100 I.U per ml of sample volume, more preferably between 1 to 60 I.U per ml of sample volume, and most preferably between 1 to 10 I.U per ml of sample volume.

It follows from the previous description that the major attainable objective of the method according to the invention is to effectively concentrate the target particle(s) or molecule(s) out of the testing sample. The concentration factor or rate is practically determined by the clot size. Therefore, in a preferred embodiment the size of the formed clot is at least $\frac{1}{3}$ of the initial sample size and preferably the clot size is less than $\frac{1}{10}$ of the initial sample volume. Moreover, in a preferred embodiment according to the invention the clot retracts to further form a small pellet with a size that my reach values that are between $\frac{1}{50}$ to $\frac{1}{1000}$ of the initial sample volume.

To attain higher retraction rate, as already described above, the concentrations of fibrinogen and thrombin are the predominant factors. Other parameters likes the calcium concentration and additives like clotting factor XIII can affect the clot size. However, in practice the clot can be further retracted in the presence of activated platelet cells or activated platelet cell lysates within the said sample. Naturally present in blood samples or as an additive in blood composite samples, the activation of the platelet can be achieved with platelet agonists selected from the group of adenosine diphosphate (ADP) and collagen.

Accordingly, the present invention discloses a method to separate target molecule(s) or particle(s) from a fibrinogen containing sample which includes the step of subjecting the said sample to activated platelet cells or platelet cell lysate. In a preferred embodiment, the said activated platelet cells or platelet cell lysate can be natively present in the said sample or artificially added to the said sample. The platelet activation is preferably achieved by ADP at a concentration of 1 mM to 1 µM and preferably between 100 µM to 10 µM.

To attain higher retraction rate, in a preferred embodiment, magnetic particles trapped in the fibrin network can be used as a retraction means to compress and therefore reduce the clot size. In practice indeed, magnetic particles will be used to emulate the role naturally played by the platelet in retracting fibrin clot. This retraction can be achieved by subjecting magnetic particles trapped within a fibrin clot to an external magnetic force. Accordingly, the said magnetic particles are trapped within the fibrin clot due to their larger size one compared with the fibrin network porosity. In a preferred embodiment, the magnetic particles are trapped within the fibrin clot by affinity interaction that the said particles may have to fibrinogen/fibrin. This can be achieved using magnetic particles coated with a fibrinogen/fibrin binding moiety that can be selected from groups of thrombin, clotting factor XIII, bacterial fibrinogen binding proteins and tissue plasminogen activator (t-PA).

To further concentrate target molecules or particles the invention further discloses the use of affinity trapping to capture the said targets within the fibrin network. The advantages of using affinity trapping are double: (1) capture small targets that are difficult or cannot be captured by size trapping within the fibrin network; (2) allow high level of concentration (i.e. very small clot or rather a pellet) of the targets as with the affinity trapping fewer fibrinogen concentration is requested to achieve efficient capture yield. In fact, with the affinity trapping one can expect to reach a concentration rate that is lower than $\frac{1}{50}$ of the initial sample volume and preferably between $\frac{1}{100}$ to $\frac{1}{1000}$ of the initial sample volume. With large sample volume (3-10 ml for instance), the concentration rate can be even less than $\frac{1}{1000}$ of the initial sample volume.

Figure 3:
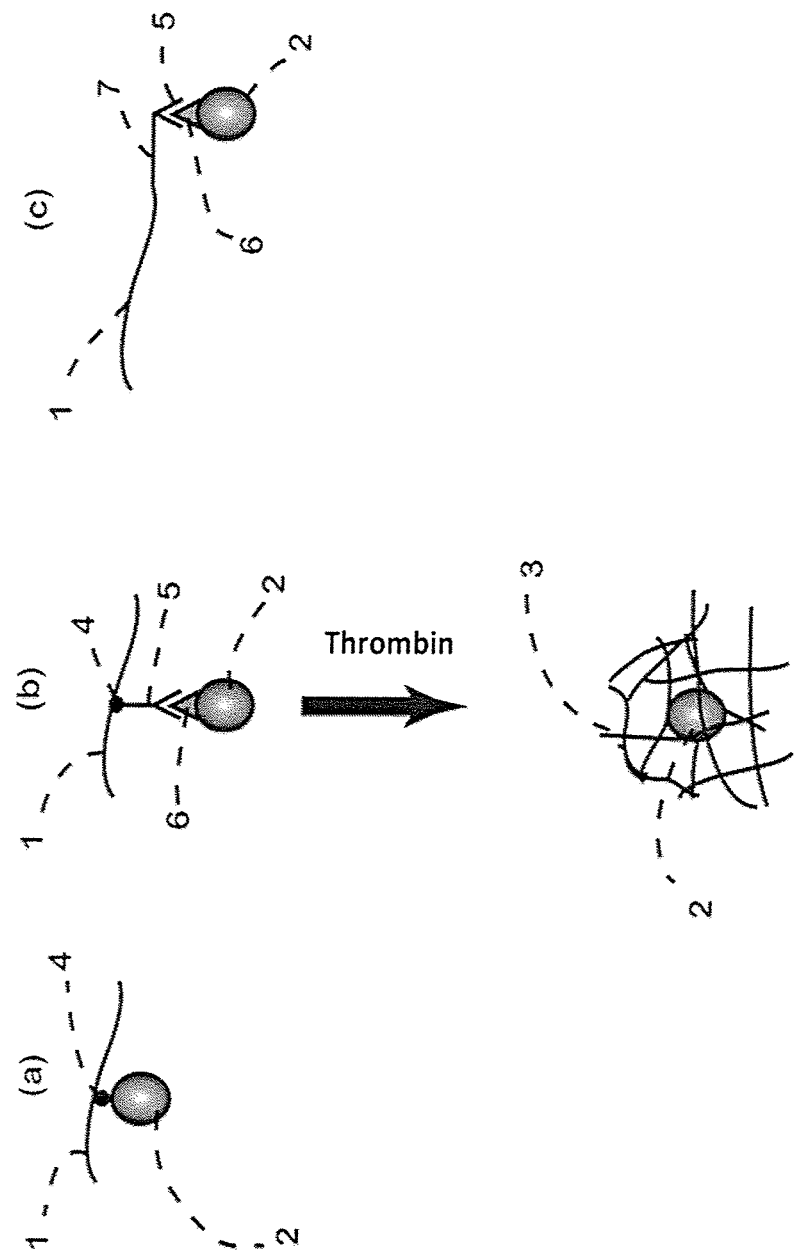
FIG. 3 is a schematic representation of different embodiments for affinity trapping of target molecule(s) or particle(s) in a fibrin network upon the exposure of a fibrinogen containing sample to thrombin: (a) native affinity of the targets (2) having a binding moiety (4) to fibrinogen/fibrin (1); (b) affinity capturing through a substance-capturing (5) directed against the said target(s) (2) and that have a fibrin/fibrinogen (1) binding moiety (4); (c) affinity capturing through a fibrinogen fusion (1) protein with a capturing moiety domain (7) directed against the target(s) (1).

As illustrated in FIG. 3 (a), in a preferred first embodiment the affinity trapping can be achieved by the native affinity of the targets (2) having a binding moiety (4) to fibrinogen/fibrin (1). A typical example of such affinity trapping is the capturing of the *staphylococcus aureus* that is known to have an effective affinity to fibrinogen/fibrin through its surface fibrinogen binding protein clumping factor A (ClfA). More generally and as exhaustively described in the international patent application WO2011/007,004, Staphylococci, Streptococci and Enterococci carry-out proteins called adhesins that can mediate infection by binding to proteins including fibrinogen. In case of blood. Another advantage of the method according to invention is the use of native affinity of blood cells to further precipitate leukocytes and thrombocytes cells within the small fibrin pellet while substantially keeping the erythrocytes in suspension. This is particularly important because micro-organisms are not always free-floating in the blood sample but are rather associated or sequestrated in the leukocytes and thrombocytes. In case of *Staphylococcus aureus* for instance, the interaction and thereafter the sequestration and bacterial survival in platelets contributes to the virulence as it allows bacteria to escape the host defenses. Native affinity capture can be also be used to capture small molecules like nucleic acids that strongly bound to fibrin due to electrical charge interaction. As for bacterial particles, the native affinity can be extended to small protein molecules as soon as such molecules have a direct interaction affinity to fibrinogen/fibrin.

In a preferred embodiment, the native affinity separation process can be adapted by using fibrinogens from different species. For instance, using sheep fibrinogens instead of human fibrinogen will lower the capture rate of *Staphylococcus aureus*. This is due to the fact that sheep fibrinogen shows a low binding affinity to *Staphylococcus aureus* bacterium. Within the same direction, the fibrinogen under use within the sample can be a recombinant or a modified fibrinogen designed to enhance or to inhibit the native affinity capture of fibrinogens to a defined targets or target groups.

A second embodiment of affinity capturing is illustrated in FIG. 3(b). Accordingly, the affinity is realized using a substance-capturing (5) directed against the said target(s) (2) and that have in turn a fibrin/fibrinogen (1) binding moiety (4). The use of a substance-capturing as an intermediate means to tag the targets is preferred in case where the target does not have a native affinity to fibrinogen/fibrin. A typical example of that is the capture of gram-negative species that in most cases lack native affinity to fibrinogen/fibrin. This can be realized, for instance, by using a gram-negative specific antibody having a fibrinogen binding moiety. Furthermore, the indirect affinity capture can be virtually extended to any target particle(s) or molecule(s) that can include but is not limited to target cells, cell components, cell subpopulations (both eukaryotic and prokaryotic), bacteria, viruses, parasites, antigens, specific antibodies, toxins, proteins, nucleic acid sequences and the like. To achieve this, the substance-capturing moiety directed against the said target molecules or particles is selected from the group comprising antibodies, nucleic acids and aptamers designed to specifically recognize the said target molecules or particles. Further, the said substance-capturing moiety can be coupled or combined with a fibrin/fibrinogen-binding moiety selected from the group comprising thrombin, fibronectin, bacterial fibrinogen binding proteins, tissue-type plasminogen activator, integrines and moieties derived from any member of this group. In a preferred embodiment, the said fibrin/fibrinogen-binding moiety and said substance-capturing moiety are covalently bound.

A third embodiment of affinity capturing is illustrated in FIG. 3(c). Accordingly, the affinity is realized using fibrinogen fusion (1) protein with a capturing moiety domain (7) directed against the target(s) (1). The use of a fusion fibrinogen protein presents the advantage of combining the selectivity of affinity capture directly within the fibrinogen molecules. Within this view, the fibrinogen molecule can be tailor made or specifically designed to specifically capture and thereafter separate one group or specific groups of targets. Moreover, the fibrinogen recombinant or modified protein can be designed to avoid native(s) interaction(s) and/or enhance specific interaction to molecules or particles within a specific sample type. Further, in another embodiment, the fibrinogen fusion protein further includes a degradation site. This will be particular useful for recovering the bound target molecules or particles out of the fibrin network during a lysis step as will be described later on. In a preferred embodiment, the degradation site is an enzymatic or hydrolytic degradation site. In a most preferred embodiment, the degradation site is an enzymatic degradation site, which is cleaved by an enzyme selected from the group consisting of plasmin and matrix metalloproteinase.

Figure 4:
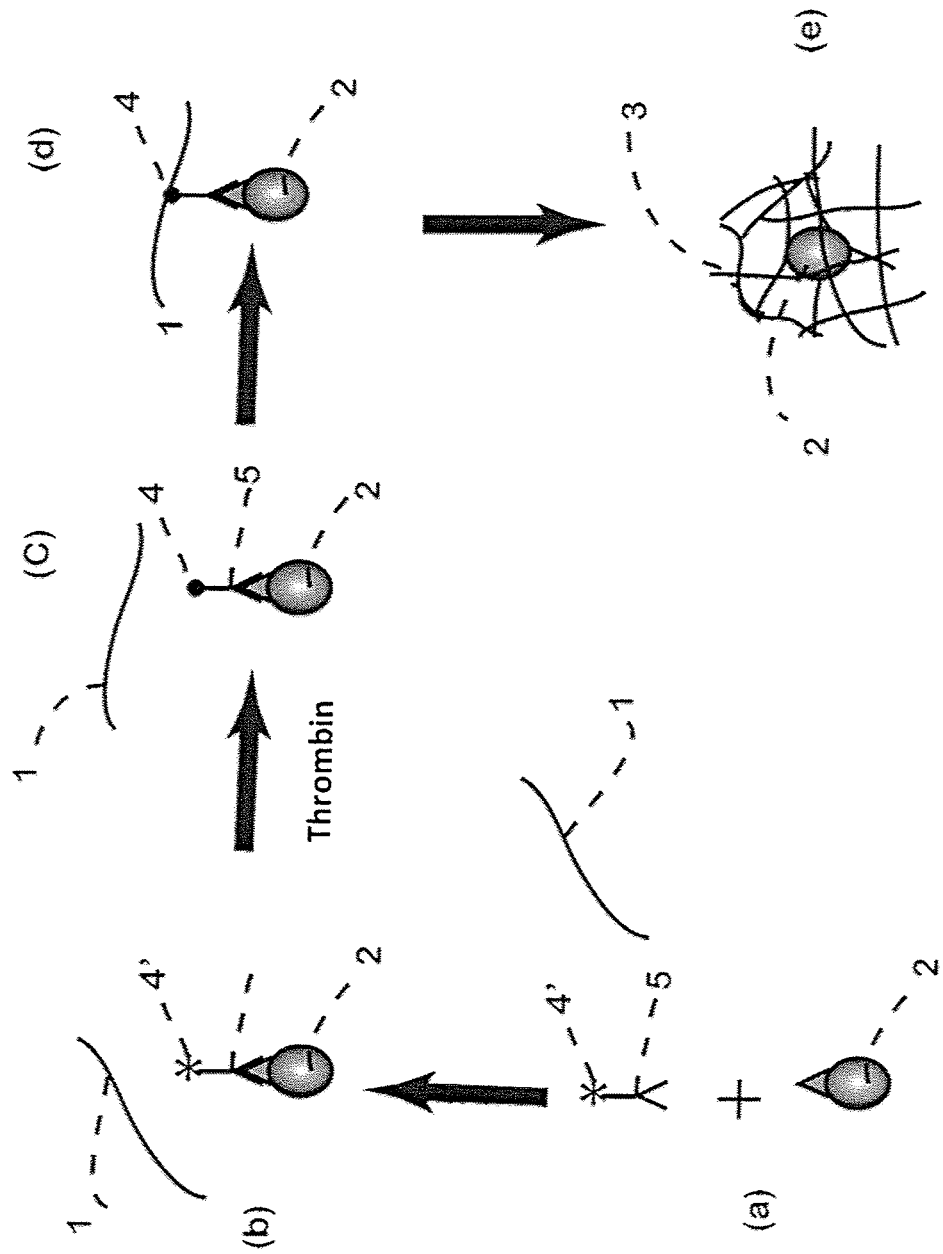
FIG. 4 is a schematic representation of a variation of the affinity trapping of FIG. 3 (b), where affinity capturing is performed through substance-capturing (5) directed against the said target(s) (2) and that have a fibrin (3) binding moiety (4'). In a preferred embodiment the affinity of the moiety (4') to fibrin will be transformed to an active form (4) only after the exposure step of the sample to Thrombin.

In a preferred embodiment and as illustrated in FIG. 4, the affinity capturing is performed through a substance-capturing (5) directed against the said target(s) (2) and that have a specific fibrin (3) binding moiety (4') without any affinity to fibrinogens like using tissue-type plasminogen activator as a fibrin binding moiety. In a preferred embodiment the affinity of the moiety (4') to fibrin will be transformed to an active form (4) only after the exposure step of the sample to Thrombin like in the case of using factor XIII as a fibrin binding moiety.

Figure 5:
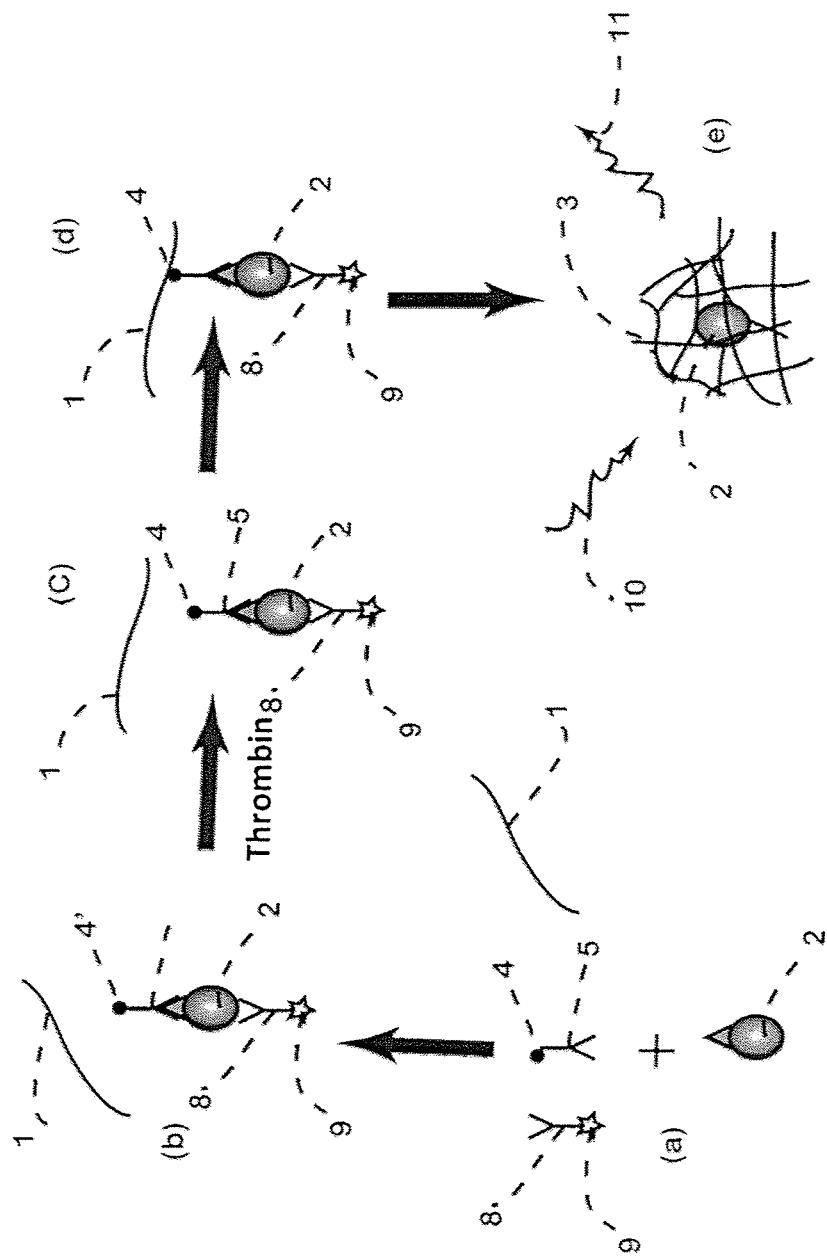
FIG. 5 is a schematic representation of a full assay processing from target separation to detection and wherein the target(s) (2) within a fibrinogen (1) containing sample is/are exposed to a substance-capturing (5) comprising fibrin/fibrinogen binding moiety (4) and a substance-labeling (8) comprising a detection label (9). Upon the exposure to thrombin the complex "target(s)/substance-capturing/substance-labeling" will be separated within a retracted fibrin clot. The detection of the target will be performed directly performed on the clot concentrate.

In use, this invention not only involves a method for separating and concentrating target molecules or particles, but it can also further include the step of detecting the said targets as illustrated in FIG. 5. With this respect, the assay processing includes the step of target capture and separation within a fibrin clot following by the detection of the said targets directly within the clot concentrate. This can be achieved for instance, by exposing the fibrinogen (1) containing sample to a substance-capturing (5) comprising fibrin/fibrinogen binding moiety (4) and a substance-labeling (8) comprising a detection label (9). This leads to the formation of a "target(s)/substance-capturing/substance-labeling". Upon the exposure to a thrombin the complex "target(s)/substance-capturing/substance-labeling" will be separated within a retracted fibrin clot (3). The detection of the target will be performed directly on the clot concentrate by for instance exposing the fibrin clot to a label (8) excitation source (10) resulting in an emission of a detection signal (11). In general the detection methodology will depend on the used label and for that well known detection methodologies as fluorescence, luminescence, SERS (Surface Enhanced Raman Spectroscopy) and Raman spectroscopy can be adopted.

After the pellet formation and target separation, in a preferred embodiment the fibrin clot or pellet can be suspended in a controlled buffered solution followed by disturbing (i.e. lysis) the clot to recover the separated target(s) from the fibrin clot. A typical example of a controlled buffer is a hypotonic buffer, buffer containing detergents in combination with fibrinolytic like plasmin and/or proteolytic agents like Proteinase K, Pronase and metalloproteinase. Such lysis step can be improved by further adding clot lysis enhancers like plasminogen or plasminogen activator. In a preferred embodiment the lysis step can further includes the use nucleic acid degradation enzymes.

For practical implementation of the invention, a second aspect of the invention concerns a sample collection device for separating target molecules or particles from a sample comprising: (i) an identification code; (ii) a container for containing the said sample that can be in form of a tube that will receive the said sample; and (iii) a fibrinogen-containing sample in the container, the device being operable to form a fibrin clot that traps in a separable manner the said target molecules or particles upon the exposure of the said sample to thrombin or a thrombin-like enzyme within the said device.

Accordingly, the volume of the said sample container is between 0.1 to 100 ml and preferably between 0.1 to 10 ml. The concentration of the said fibrinogen in the sample is preferably at least 0.1 µg/ml. In a preferred embodiment the concentration of the fibrinogen in the sample is between 0.1 to 100 mg/ml and most preferably between 10 mg/ml to 10 µg/ml.

Accordingly, the said device further includes as an additive a thrombin or thrombin enzyme. With this respect, the thrombin concentration is 0.01 to 10 I.U/ml and preferably within the range of 0.1 to 2 I.U/ml of sample. In practice, the quantity of the thrombin or thrombin like enzyme must be rather adjusted in correspondence to the fibrinogen concentration within the device to obtain the desired fibrin network structure and clot size. With this respect, the thrombin amount is preferably less than 20 I.U thrombin per mg of fibrinogen, preferably in a range between 0.01 to 10 I.U thrombin per mg of fibrinogen, more preferably between 0.1 to 1 I.U thrombin per mg of fibrinogen.

In case of blood samples as whole blood for instance, sample collection device according to the invention further includes coagulation agents that promote the generation of endogenous thrombin within the sample. Such promoting agents can be for instance selected from groups comprising powderous or fibrous silicate compounds such as kaolin, Celite, diatomaceous silica and glass fibers, fine powders of calcium compounds such as calcium carbonate and calcium sulfate, thrombin-like substances derived from snake venoms, and polyphenols that can activate blood clotting factors to promote the coagulation. Further, these coagulation promoting agents can be, for example, added individually or in combination into the sample or coated inside the wall of sample container. The amount and the process of which, the said endogenous thrombin promoting agents must be adjusted in a way to control the coagulation process and obtain a small fibrin clot size.

Further, the device according to the invention may include additives selected from the group of calcium, chelating agents, activated platelet cells or activated platelet cell lysate and factor XIII. Accordingly, the sample collection device may further include as an additive magnetic particles. In a preferred embodiment the said magnetic particle within the device are coated with a fibrinogen/fibrin binding moiety selected from the group comprising thrombin, fibronectin, bacterial fibrinogen binding proteins, tissue-type plasminogen activator, integrines and moieties derived from any member of this group. In a preferred embodiment, the said fibrin/fibrinogen-binding moiety and said magnetic particles are covalently bound.

Further, the device according to the invention may include additives comprising molecules having: (I) fibrin/fibrinogen-binding moiety and (II) a substance-capturing moiety directed against the said target molecules or particles. Accordingly, the said substance-capturing moiety directed against the said target molecules or particles can be selected from the group comprising antibodies, nucleic acids and aptamers designed to specifically recognize the said target molecules or particles. Further, the said substance-capturing moiety can be coupled or combined with a fibrin/fibrinogen-binding moiety selected from the group comprising thrombin, fibronectin, bacterial fibrinogen binding proteins, tissue-type plasminogen activator, integrines and moieties derived from any member of this group. In a preferred embodiment, the said fibrin/fibrinogen-binding moiety and said substance-capturing moiety are covalently bound.

Further, the device according to the invention can include additives comprising a fibrinogen recombinant or modified protein. Such recombinant or modified fibrinogen protein can be specifically designed to enhance or inhibit affinity interactions of the said recombinant fibrinogen protein with specific target molecules or particles contained in the sample under use within the device. In a preferred embodiment, the said recombinant protein in use within the device is a fibrinogen fusion protein with a capturing moiety domain directed against the said target molecules or particles. In another embodiment, the fibrinogen fusion protein further includes a degradation site. This will be particular useful for recovering the bound target molecules or particles out of the fibrin network during a lysis step as it will be described later on. In a preferred embodiment, the degradation site is an enzymatic or hydrolytic degradation site. In a most preferred embodiment, the degradation site is an enzymatic degradation site, which is cleaved by an enzyme selected from the group consisting of plasmin and matrix metalloproteinase.

In practice all of the previously described additives can be added to the sample after the sample collection or already integrated within the device. In the last case, the additives can be integrated solubilised in an aqueous buffer solution. Preferably, the said buffer comprises water, calcium chloride, preferably at a concentration of 40 mM, and sodium chloride, preferably at a concentration of 75 mM, and has preferably a pH of 7.3. In a preferred embodiment, the said additives can be included within the device in a lyophilized format that can be solubilised just prior to the device use or upon the introduction of the sample within the device.

The so disclosed device for sample collection will in operation lead to the formation of a small fibrin clot in which target particles or molecules are trapped. The concentration factor or rate is practically determined by the clot size. Therefore, the device composition and design so that it will result to the formation of a clot with a size that is at least $\frac{1}{3}$ of the initial sample size and preferably the clot size is at least $\frac{1}{10}$ of the initial sample volume. Moreover, in a preferred embodiment according to the invention the clot retracts to further form a small pellet with a size that may reach values that are between $\frac{1}{50}$ to $\frac{1}{1000}$ of the initial sample volume.

The sample collection device according to the invention can be used to separate and concentrate target molecules or particles that can be selected from groups comprising target cells, cell components, cell subpopulations (both eukaryotic and prokaryotic), bacteria, viruses, parasites, antigens, specific antibodies, toxins, proteins, nucleic acid sequences and the like.

The sample collection device according to the invention can be used to separate and concentrate target molecules or particles from diverse samples as already defined. In general this includes whole blood, blood derivatives, blood components, composed samples with clotting factors additives. With this respect, the sample herein can refer to any sample type that need to be tested including food, clinical, environmental, and experimental samples.

In practice the identification code within the device can be for instance a code bar, color, size and shape of the device. Such identification code can be used as a reference or indicator the device intended use and application. The devices according to the invention can be, in fact, differentiated according to their composition, sample type for which the device will be used and or the target(s) that need to be separated.

Figure 6:
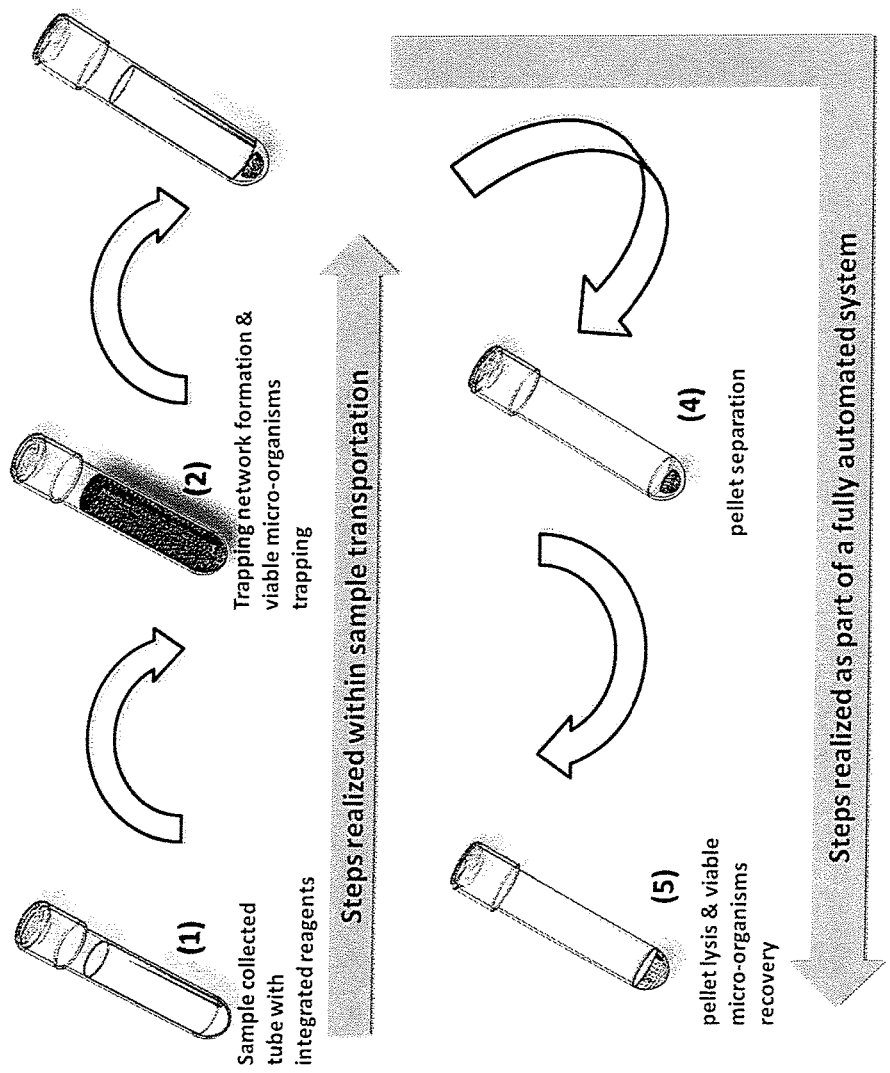
FIG. 6 is a schematic representation of a sample collection device operation; according to the invention the device is being operable to form a fibrin clot that traps in a separable manner the said target molecules or particles upon the exposure of the said sample to thrombin or a thrombin-like enzyme within the said device.

FIG. 6 shows an example of a sample processing using a device according to the invention. The device can be a standard reaction tube with a closing cap and an identification code. The device is designed to receive a fluid sample that needs to be thereafter examined for the existence of target particle(s) or molecule(s) as for instance a pathogenic particle(s) (bacteria, viruses etc.) or target molecule(s) (DNA, RNA or protein etc.). The device of the invention will further include stable reagent formulations that will lead to the fibrin clot formation and targets separation. Upon the sample collection within the device, the fibrinogen molecules will first react with the targets inside the tube. In a second step the fibrinogen will be transformed to a fibrin, leading to a polymerization and trapping of said targets in the fibrin network. The fibrin network in a third step will retract to form a small pellet within the blood container. As the pellet will be formed, the surrounding sample will be decanted leading to separation of the targets trapped within this small pellet. In a final step, the pellet can be lysed to recover the targets from their fibrin trap within a small volume of a controlled buffer. While the target trapping/pellet formation step will be performed in a closed tube during the sample transportation for instance, the pellet separation and lysis can be easily performed using a state-of-art liquid handling automated system. With this process, the disclosed device will allow to collect the sample and at the same time to effectively separate and concentrate targets particles or molecules out of the said sample, considerably simplifying the necessary sample processing steps and further result in a reduction of potential risks of infection and risks of contamination.

Example 1

Capture of *Staphylococcus aureus* (SA) bacterium from a blood component sample: Platelet Rich Plasma (PRP) sample. A sample of 500 µl of citrated PRP is spiked with 100 CFU of a SA bacterium. By adding 5 µl of Thrombin at a concentration of 10 U.I./ml and incubation, a small pallet (10-20 µl size) will be formed. The lysis of the so-formed pallet using a 100 µl lysis buffer (0.01% Saponin, 0.05% Tween and 0.05% Triton X) and 5 µl of Proteinase K (10 U.I./ml) leads to recovery of between 90-100% of initially spiked SA bacterium in the lysis buffer.

Example 2

Capture of *Staphylococcus aureus* (SA) bacterium from a blood component sample: Platelet Poor Plasma (PPP) sample. A sample of 500 µl of citrated PPP is spiked with 100 CFU of a SA bacterium and processed using the same protocol as for Example 1. The same recovery performance will be obtained. However, the size of the fibrin clot is larger when compared with the PRP case. This difference is due to the low retraction of the Fibrin clot in case of the PPP sample. This retraction is instead assured by the platelets cells present within the PRP sample.

Example 3

Capture of Staphylococcus aureus (SA) bacterium from a blood component sample: Serum sample. A sample of 500 μl of citrated serum is spiked with 100 CFU of a SA bacterium and processed using the same protocol as for Example 1. In this case no clot/pellet will be formed due to lack on fibrinogen within the serum sample. By adding 1.25 mg of human Fibrinogen to the serum sample, one will be able to form the fibrin clot and thereby separate the SA bacterium out of the serum sample.

Example 4

Capture of gram-positive bacterium and Fungi out of whole blood. Recovery from 4 ml whole blood spiked with 100 CFU of micro-organisms:

| Micro-organisms strain/species | Yield |
|---|---|
| S. pyogenes M57 | 85% |
| C. albicans | 92% |
| MRSE | 83% |
| E. faecalis | 70% |

Example 5

Specific capture of bacterium out of a composed sample. 1 ml of a composed PBS samples are spiked with *Staphylococcus aureus* (SA) (1000 CFU/ml) or *Citrobacter Freundi* (18000 CFU/ml) at different concentrations of fibrinogen within the sample:

| Fibrinogen (mg/ml) | 2.5 | 1.25 | 0.625 | 0.312 | 0.156 | 0.08 |
|---|---|---|---|---|---|---|
| Pellet volume (concentration rate) | ~200 μl (1/5) | | | | | <1 μl (1/1000) |
| Yield MRSA MW2 in % (1000 cfu/ml) | 100 | 100 | 100 | 100 | 100 | 100 |
| Citrobacter freundi in % (1800 CFU/ml) | 48 | 44 | 34.7 | 7.6 | 0 | 0 |

By reducing the fibrinogen concentration, one will reduce the pallet size (i.e. concentration rate) and by the way the fibrin network porosity size. In such conditions, the SA capture rate is still very efficient while the *C. Freundi* capture rate will be considerably reduced. This different of capture efficiency is due to the fact that the SA bacterium has a strong native affinity to fibrinogen (through its ClfA surface protein) while the *C. Freundi* lacks such affinity.

Example 6

Specific capture of bacterium out a composed sample. The same conditions as for Example 5 using *C. Freundi* within a 1 ml composed PBS as a sample with the modification that we further added to the sample an antibody directed against gram-negative lipid-A surface protein labeled with a staphylococcal ClfA protein. In this condition and as shown in FIG. 3(*b*), the antibody will bind *C. Freundi* allowing its effective binding to fibrinogen and thereafter its efficient separation (nearly 100% yield) within a fibrin pellet.

Those skilled in the art will appreciate that various adaptations and modifications of the just-described preferred embodiments can be configured without departing from the scope and spirit of the invention. Therefore, it is to be understood that, within the scope of the appended claims, the invention may be practiced otherwise than as specifically described herein.

The invention claimed is:

1. A method for separating target molecules or particles from a blood sample containing fibrinogen, wherein said blood sample comprises an exogenously-added chelating agent comprising:
   a. trapping said target molecules or particles in a fibrin network by contacting the blood sample with an exogenous thrombin or thrombin-like enzymes in an amount sufficient to convert at least partially the fibrinogen contained in the blood sample into fibrin to form the fibrin network
   b. retracting said fibrin network to form a fibrin clot with a size less than $\frac{1}{10}^{th}$ of the initial volume size; and
   c. separating said fibrin clot from the surrounding blood sample.

2. The method according to claim 1, wherein the concentration of the fibrinogen within the blood sample is at least 1 μg/ml.

3. The method according to claim 2, wherein the concentration of said thrombin or thrombin-like enzyme is between 0.01 to 10 IU per milliliter of sample.

4. The method according to claim 1, wherein the blood sample further contains clotting factor XIII.

5. The method according to claim 1, wherein the blood sample further contains calcium.

6. The method according to claim 1, wherein the chelating agents is selected from the group consisting of GDTA, EDTA and citrate.

7. The method according to claim 1, wherein the blood sample further includes activated platelet cells or activated platelet cell lysate within said blood sample.

8. The method according to claim 7, wherein the platelets are activated with platelet agonists selected from the group consisting of adenosine diphosphate and collagen.

9. The method according to claim 1 which further includes the step of lysing said fibrin clot to recover said target molecules or particles.

10. The method according to claim 9, wherein the step of lysing said clot is performed using fibrinolytic agents.

11. The method according to claim 9, wherein said lysing step uses components selected from the group consisting of cytolysis, proteases and nucleic acid degradation enzymes.

12. The method according to claim 9, wherein the said lysing step includes the use of detergents.

13. The method according to claim 1, wherein said blood sample is selected from the group consisting of whole blood, platelet-rich plasma, platelet-poor plasma and serum.

14. The method according to claim 1, wherein said blood sample is an artificially composed blood sample obtained by combining a blood sample with a fibrinogen deficient sample.

15. The method according to claim 1, wherein said blood sample is an artificially composed blood sample obtained by combining clotting factors with a fibrinogen deficient sample.

16. The method according to claim 15, wherein said clotting factor is fibrinogen.

17. The method according to claim 1, wherein trapping in step a) is obtained by size trapping said target particles or molecules within the fibrin network.

18. The method according to claim 1, wherein trapping in step a) is obtained by affinity trapping, said target particles or molecules within the fibrin network.

19. The method according to claim 18, wherein trapping is realized by a native affinity of said target molecules or particles to fibrinogen or fibrin.

20. The method according to claim 19, wherein the trapping comprises a molecule composed from: (i) a fibrin/fibrinogen-binding moiety and (ii) a substance-capturing moiety directed against said target molecules or particles.

21. The method according to claim 19, wherein the fibrinogen is a fibrinogen fusion protein with a capturing moiety domain directed against said target molecules or particles.

22. The method according to claim 20, wherein a fibrin/fibrinogen-binding moiety is selected from the group consisting of thrombin, fibronectin, bacterial fibrinogen binding proteins, tissue-type plasminogen activator, integrines and moieties derived from any member of this group.

23. The method according to claim 20, wherein a substance-capturing moiety directed against said target molecules or particles is selected from the group consisting of antibodies, nucleic acids and aptamers designed to specifically recognize the said target molecules or particles.

24. The method according to claim 1, wherein said target molecules or particles comprise bacteria, virus, yeast, proteins, peptides, and/or nucleic acids.

* * * * *

UNITED STATES PATENT AND TRADEMARK OFFICE
CERTIFICATE OF CORRECTION

PATENT NO. : 9,689,881 B2  
APPLICATION NO. : 13/822209  
DATED : June 27, 2017  
INVENTOR(S) : Rida et al.

Page 1 of 1

It is certified that error appears in the above-identified patent and that said Letters Patent is hereby corrected as shown below:

On the Title Page

Assignee: Change "SPINOMIX S.A." to "DEBIOPHARM INTERNATIONAL SA"

Signed and Sealed this  
Twenty-ninth Day of August, 2017

Joseph Matal  
*Performing the Functions and Duties of the*  
*Under Secretary of Commerce for Intellectual Property and*  
*Director of the United States Patent and Trademark Office*